US008083344B2

(12) United States Patent
Blanshay et al.

(10) Patent No.: US 8,083,344 B2
(45) Date of Patent: Dec. 27, 2011

(54) PROTECTIVE EYEWEAR INCLUDING AUXILIARY LENSES

(75) Inventors: Jonathan Blanshay, Montreal (CA); Brent Sheldon, Montreal (CA); Pierre Vallée, Saint-Julie (CA); Stéphane Morency, Montreal (CA); Christian Pilon, Montreal (CA); Stéphane Beliveau, Montreal (CA); Catherine Turgy, Montreal (CA)

(73) Assignee: Revision Military Inc., Montreal, Quebec (CA)

( * ) Notice: Subject to any disclaimer, the term of this patent is extended or adjusted under 35 U.S.C. 154(b) by 0 days.

(21) Appl. No.: 12/634,443

(22) Filed: Dec. 9, 2009

(65) Prior Publication Data
US 2010/0195043 A1 Aug. 5, 2010

Related U.S. Application Data

(62) Division of application No. 11/435,546, filed on May 17, 2006, now Pat. No. 7,648,233.

(60) Provisional application No. 60/681,610, filed on May 17, 2005, provisional application No. 60/722,575, filed on Oct. 1, 2005.

(51) Int. Cl.
*G02C 11/08* (2006.01)
(52) U.S. Cl. .............................. 351/62; 2/436
(58) Field of Classification Search .................. 351/62, 351/158, 41; 2/436
See application file for complete search history.

(56) References Cited

U.S. PATENT DOCUMENTS

| 2,085,844 | A | 7/1937 | Baker |
| 2,364,584 | A | 12/1944 | Malcom |
| 2,410,184 | A | 10/1946 | Schauweker |
| 2,435,243 | A | 2/1948 | Splaine |
| 2,846,684 | A | 8/1958 | Hill |
| 3,000,011 | A | 9/1961 | Bright |
| 3,012,248 | A | 12/1961 | Maurice |
| 3,031,675 | A | 5/1962 | Dubach |
| 3,051,957 | A | 9/1962 | Chan |
| 3,368,221 | A | 2/1968 | Anderson |
| 3,395,406 | A | 8/1968 | Smith |
| 3,418,658 | A | 12/1968 | Danico |
| 3,517,393 | A | 6/1970 | Beauchef |
| 3,563,640 | A | 2/1971 | Buban |
| 3,708,224 | A | 1/1973 | Lindblom |
| 3,718,937 | A | 3/1973 | Smith |

(Continued)

OTHER PUBLICATIONS

Ski, p. 194-195, Nov. 2002.

(Continued)

*Primary Examiner* — Hung Dang
(74) *Attorney, Agent, or Firm* — Erickson Law Group, PC

(57) ABSTRACT

An eyewear assembly includes an outer first frame, at least one outer first lens, an inner second frame, and at least one inner second lens. The assembly includes a mechanism for holding the first frame and first lens in front of a user's face. The second frame has a mechanism for attachment to the first frame, to hold the second frame between the user's eyes and the first lens. The at least one second lens is carried by the second frame. The mechanism for attachment comprises a tab extending vertically on one of the first frame or the second frame and an aperture on the respective other of the first frame or the second frame for receiving said tab. The first frame includes a central elevated vent to distribute air over top vent openings of the first frame. Grip warts are provided on the first frame for gripping and manipulation by the user.

13 Claims, 22 Drawing Sheets

U.S. PATENT DOCUMENTS

| | | | |
|---|---|---|---|
| 3,787,113 A | 1/1974 | Shedrow |
| 3,945,044 A | 3/1976 | McGee et al. |
| 4,176,410 A | 12/1979 | Matthias |
| 4,264,988 A | 5/1981 | Specht |
| 4,271,538 A | 6/1981 | Montesi |
| 4,425,669 A | 1/1984 | Grendol et al. |
| 4,435,852 A | 3/1984 | Nesler |
| D273,819 S * | 5/1984 | Yehl |
| 4,447,914 A | 5/1984 | Jannard |
| 4,556,995 A | 12/1985 | Yamamoto |
| 4,607,398 A | 8/1986 | Faulconer |
| 4,618,225 A | 10/1986 | Shedrow |
| 4,649,577 A | 3/1987 | Wiedner |
| 4,670,914 A | 6/1987 | Harris |
| D290,710 S * | 7/1987 | Aliberti |
| 4,689,838 A | 9/1987 | Angermann et al. |
| 4,711,539 A | 12/1987 | Krusas et al. |
| RE32,638 E | 4/1988 | Nesler |
| 4,785,481 A | 11/1988 | Palmer |
| 4,810,080 A | 3/1989 | Grendol et al. |
| 4,877,320 A | 10/1989 | Holden |
| 4,964,714 A | 10/1990 | Weymouth et al. |
| 4,977,627 A | 12/1990 | Metcalfe et al. |
| 5,018,223 A | 5/1991 | Dawson et al. |
| 5,027,443 A | 7/1991 | Watkins |
| D327,490 S * | 6/1992 | Wilson |
| D328,084 S * | 7/1992 | Salce et al. |
| 5,170,502 A | 12/1992 | Hegendorfer et al. |
| 5,189,447 A | 2/1993 | Oleson |
| 5,191,364 A | 3/1993 | Kopfer |
| 5,239,320 A | 8/1993 | Allendorf |
| D339,364 S * | 9/1993 | Bolle |
| D351,850 S * | 10/1994 | Bolle |
| 5,363,512 A | 11/1994 | Grabos |
| 5,371,555 A | 12/1994 | Nagel |
| D358,159 S * | 5/1995 | Lai |
| 5,410,763 A | 5/1995 | Bolle |
| 5,412,438 A | 5/1995 | Bolle' |
| 5,428,407 A | 6/1995 | Sheffield |
| 5,428,411 A | 6/1995 | Kopfer |
| 5,542,130 A | 8/1996 | Grabos |
| 5,576,775 A | 11/1996 | Bolle |
| 5,608,470 A | 3/1997 | Sheffield |
| 5,610,668 A | 3/1997 | Mage |
| 5,617,588 A | 4/1997 | Canavan |
| 5,638,145 A | 6/1997 | Jannard et al. |
| 5,652,965 A | 8/1997 | Crooks |
| 5,657,106 A | 8/1997 | Herald et al. |
| 5,689,834 A | 11/1997 | Wilson |
| 5,711,035 A | 1/1998 | Haslbeck |
| 5,771,499 A | 6/1998 | Monaco et al. |
| 5,790,230 A | 8/1998 | Sved |
| 5,801,805 A | 9/1998 | Mage |
| 5,802,622 A | 9/1998 | Baharad et al. |
| 5,815,235 A | 9/1998 | Runckel |
| D400,905 S * | 11/1998 | Wang |
| 5,841,506 A | 11/1998 | Karasawa et al. |
| D405,102 S * | 2/1999 | Moritz et al. |
| 5,867,841 A | 2/1999 | Chiang |
| 5,898,468 A | 4/1999 | Mage |
| 5,907,384 A | 5/1999 | Kirsch et al. |
| 5,929,963 A | 7/1999 | McNeal |
| 5,956,115 A | 9/1999 | Bolle |
| 5,969,787 A | 10/1999 | Hall et al. |
| 6,009,564 A | 1/2000 | Tackles et al. |
| 6,047,410 A | 4/2000 | Dondero |
| 6,049,917 A | 4/2000 | Ryden |
| 6,050,684 A | 4/2000 | Mage |
| 6,076,196 A | 6/2000 | Masumoto |
| D428,039 S | 7/2000 | Thixton |
| 6,116,731 A | 9/2000 | Fuchs |
| 6,119,276 A | 9/2000 | Newcomb et al. |
| 6,138,285 A | 10/2000 | Robrahn et al. |
| 6,138,286 A | 10/2000 | Robrahn et al. |
| D439,267 S * | 3/2001 | Hussey |
| 6,206,519 B1 | 3/2001 | Lin |
| 6,233,342 B1 | 5/2001 | Fernandez |
| 6,276,795 B1 | 8/2001 | Hall et al. |
| 6,282,727 B1 | 9/2001 | Lindahl |
| 6,386,703 B1 | 5/2002 | Huang |
| 6,427,254 B1 | 8/2002 | Gardner |
| 6,502,937 B2 | 1/2003 | Yang |
| 6,550,914 B1 | 4/2003 | Kopfer |
| D477,010 S | 7/2003 | Moritz et al. |
| 6,601,240 B2 | 8/2003 | Tsubooka |
| 6,611,965 B1 | 9/2003 | Lee |
| 6,611,966 B1 * | 9/2003 | Yamamoto et al. ............ 2/436 |
| 6,615,409 B2 | 9/2003 | Youmans |
| 6,637,038 B1 * | 10/2003 | Hussey ............................ 2/436 |
| 6,637,877 B1 | 10/2003 | Hartley et al. |
| 6,641,263 B2 | 11/2003 | Olney |
| 6,665,885 B2 | 12/2003 | Masumoto |
| 6,694,532 B2 | 2/2004 | Chen |
| D488,182 S * | 4/2004 | Sheldon et al. |
| 6,715,157 B2 | 4/2004 | Mage |
| 6,718,561 B2 | 4/2004 | Dondero |
| 6,732,382 B2 | 5/2004 | Dondero |
| 6,732,383 B2 | 5/2004 | Cleary et al. |
| 6,749,299 B1 | 6/2004 | Hsu |
| D493,189 S | 7/2004 | Canavan |
| 6,772,448 B1 | 8/2004 | Hockaday et al. |
| 6,783,235 B1 | 8/2004 | Lin |
| 6,923,537 B2 | 8/2005 | Hartley et al. |
| 6,928,663 B1 | 8/2005 | Tappeiner |
| D510,378 S | 10/2005 | Dondero et al. |
| D537,099 S | 2/2007 | Saderholm et al. |
| D537,100 S | 2/2007 | Moritz et al. |
| 7,181,779 B2 | 2/2007 | Hussey |
| D538,834 S | 3/2007 | Mangum |
| D541,328 S | 4/2007 | Saderholm et al. |
| 2002/0023292 A1 | 2/2002 | Masumoto |
| 2004/0103469 A1 | 6/2004 | Hussey |
| 2004/0117898 A1 | 6/2004 | Penque, Jr. et al. |
| 2005/0015864 A1 | 1/2005 | Chen |
| 2005/0160521 A1 | 7/2005 | Hussey |
| 2005/0193478 A1 | 9/2005 | Hussey |

OTHER PUBLICATIONS

Ski, p. 158, 161, Nov. 1997.
Ski, p. 159, 162, Dec. 2002.
Ski, p. 180, Sep. 2005.

* cited by examiner

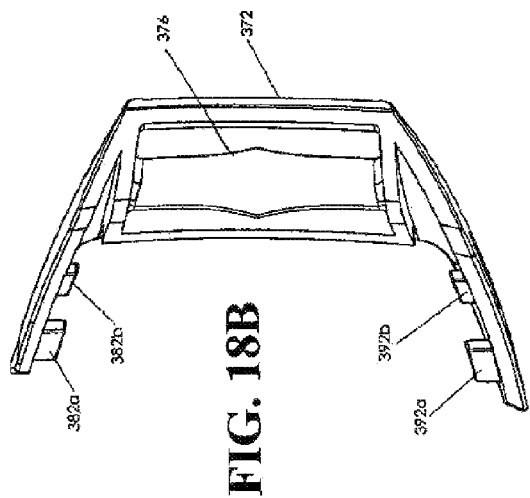
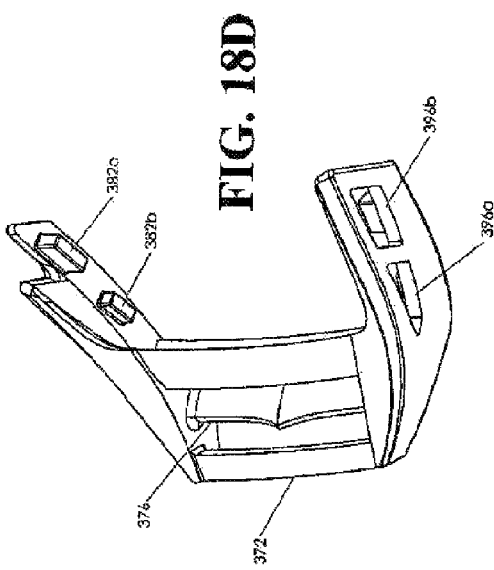
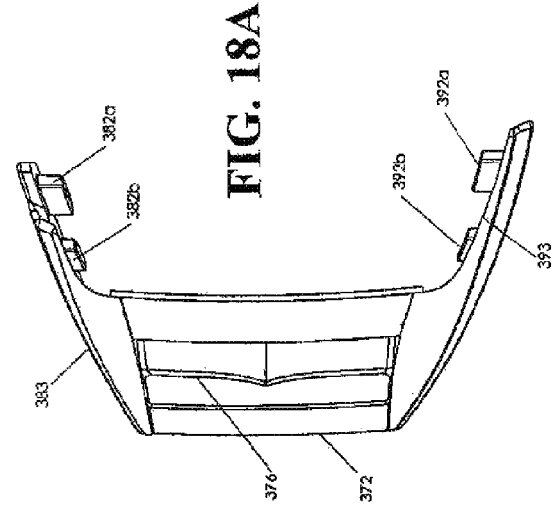
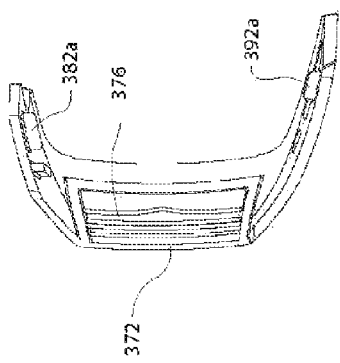

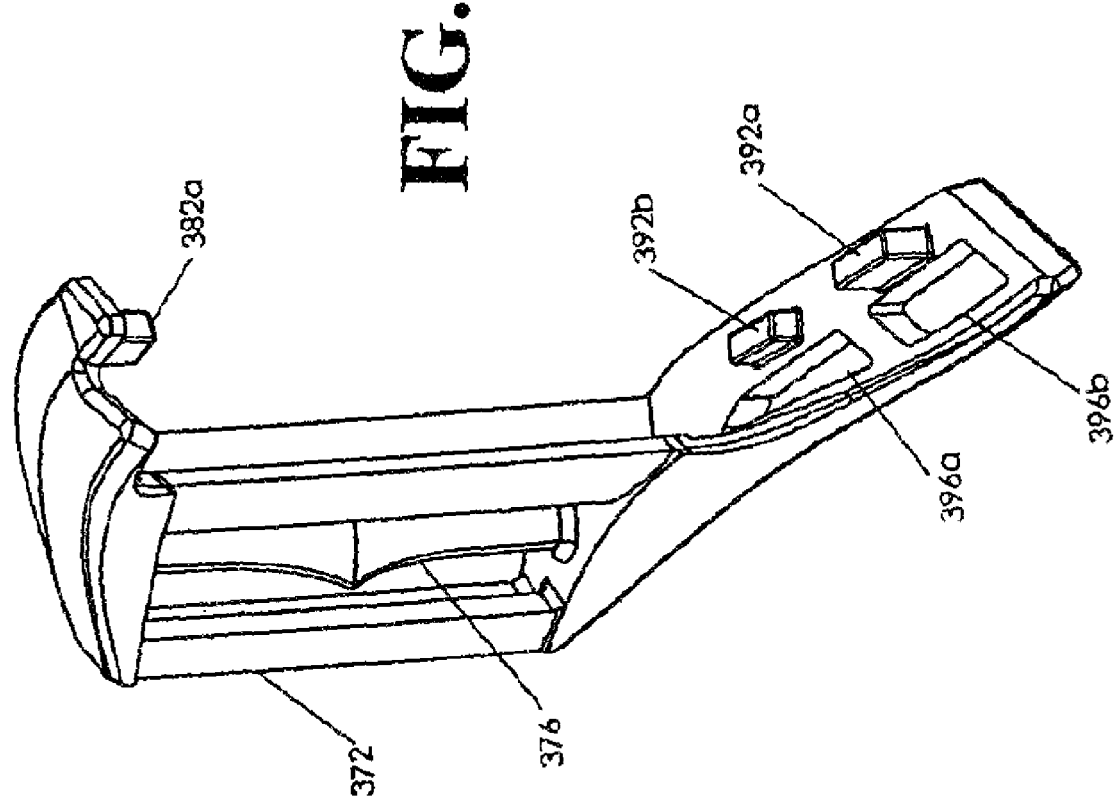

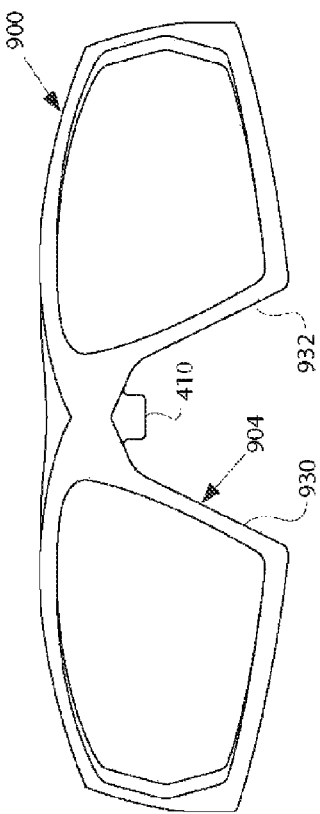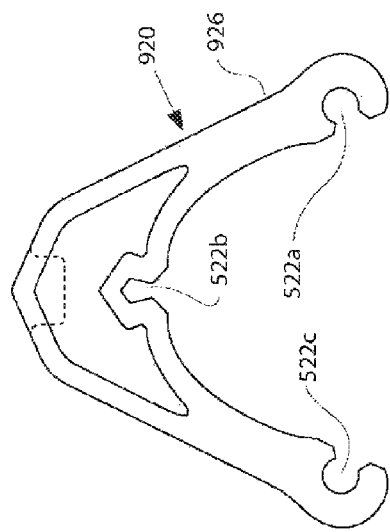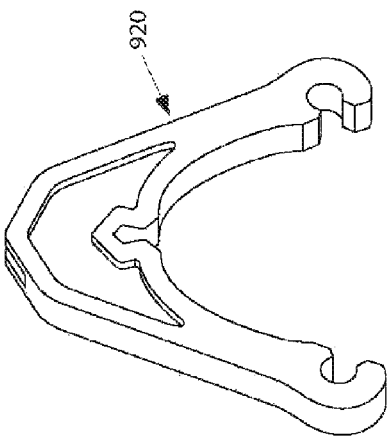

PROTECTIVE EYEWEAR INCLUDING AUXILIARY LENSES

This application is a divisional of U.S. patent application Ser. No. 11/435,546 filed on May 17, 2006, now U.S. Pat. No. 7,648,233, which claims the benefit of U.S. provisional application Ser. Nos. 60/681,610 filed May 17, 2005 and 60/722,575 filed Oct. 1, 2005.

TECHNICAL FIELD OF THE INVENTION

The present invention relates to eyewear, particularly to ballistic protective eyewear, provisions provided by the protective eyewear to mount inner lenses, and ventilation and structure of protective eyewear frames.

BACKGROUND OF THE INVENTION

Specially adapted, protective eyewear is used today by soldiers and law enforcement officers. The use of such eyewear is particularly advantageous in harsh environments where sunlight, wind, dust and debris can be hazardous to eyesight. Additionally, such eyewear can be designed to protect the eyes against some level of impact of fragments and projectiles during battle. Such eyewear includes the Sawfly™ shield, Bullet Ant™ goggles or Desert Locust™ goggles available from Revision Military of Montreal, Canada, or Revision Eyewear, Ltd. of Williston, Vt., USA.

Provisions have been made in protective eyewear for adapting the eyewear to accept a prescription lens assembly behind the outer protective lens of the eyewear. U.S. Pat. Nos. 5,790,230; 5,412,438 and 4,810,080 describe such provisions.

The present inventors have recognized that such systems can be improved to achieve additional benefits. The present inventors have recognized that it would be advantageous to provide an inner lens sub-assembly, such as for prescription lenses, for fitment to protective eyewear wherein the inner lens subassembly is shatter resistant, prevents scratching of the protective eyewear lens by the inner lens sub-assembly, ensures an air passage between the inner and outer lenses, and is more easily finger manipulated by the user.

The present inventors have recognized that it would be desirable to provide a protective eyewear, such as goggles, that improved ventilation through the eyewear to prevent fogging of the protective eyewear lens. The present inventors have recognized that it would be desirable to provide protective eyewear that is easily assembled, cost effectively manufactured, reliable, and conforms comfortably to the user's face, and is easily manipulated and handled by the user.

SUMMARY OF THE INVENTION

An exemplary embodiment of the present invention provides a protective eyewear assembly that includes an inner lens sub-assembly for fitment to protective eyewear that is shatter resistant, that prevents scratching of the outer protective eyewear lens by the inner lens sub-assembly, and that is more easily finger manipulated by the user. The present invention provides at least two types of outer protective eyewear that are configured to receive and mount the same inner lens sub-assembly.

According to one embodiment an outer protective lens is incorporated into a shield-type eyewear. According to another embodiment the outer protective lens is incorporated into a pair of goggles. An inner lens sub-assembly, including frame and lens, is configured to be fit and mounted into either embodiment. The inner lens sub-assembly is thus a universal part, compatible with either embodiment. A cost and convenience advantage is achieved for the manufacturer and the user.

According to another aspect of the invention, protective goggles are provided that include a multi-component frame comprising a soft frame which holds a protective lens and which conforms to a user's face, and two relatively rigid strap anchor portions mounted on either side of the frame. The strap anchor portions include a mechanism for engaging a strap for mounting the protective goggles to the user's face and inwardly directed louvers for directing air toward side ventilation openings of the frame.

According to another aspect of the invention, protective goggles are provided that include a frame surrounding a protective lens, the frame having a central vent opening in a top region wherein the central vent opening allows air to pass through the frame to an open region above top ventilation openings through the frame. The goggles further include louvers on opposite sides thereof, the louvers directing air toward side ventilation openings for the frame.

According to another aspect of the invention, the protective goggles include grip warts or bumps that assist in gripping and manipulation of the goggles by a user. The grip warts can be extensions of the soft goggle frame material that are exposed through openings provided in the strap anchor portions. The grip warts can serve the dual purpose of providing a user gripping function and assisting in the securement of the strap anchor portions to the rest of the goggle frame.

Numerous other advantages and features of the present invention will be become readily apparent from the following detailed description of the invention and the embodiments thereof, the claims and from the accompanying drawings.

BRIEF DESCRIPTION OF THE DRAWINGS

FIG. 18A is a front view of a strap anchor taken from FIG. 10;

FIG. 18B is a rear view of the strap anchor taken from FIG. 18A;

FIG. 18C is a slight perspective view of the strap anchor taken from FIG. 18A;

FIG. 18D is a right side perspective view of the strap anchor taken from FIG. 18A, tipped upward;

FIG. 18E is a right side perspective view of the strap anchor taken from FIG. 18A, tipped downward;

FIG. 32 is a front view of an alternate embodiment auxiliary frame;

FIG. 33 is a perspective view of an alternate goggle adapter; and

FIG. 34 is a front view of the goggle adapter of FIG. 33.

DESCRIPTION OF THE PREFERRED EMBODIMENTS

Figure 1:
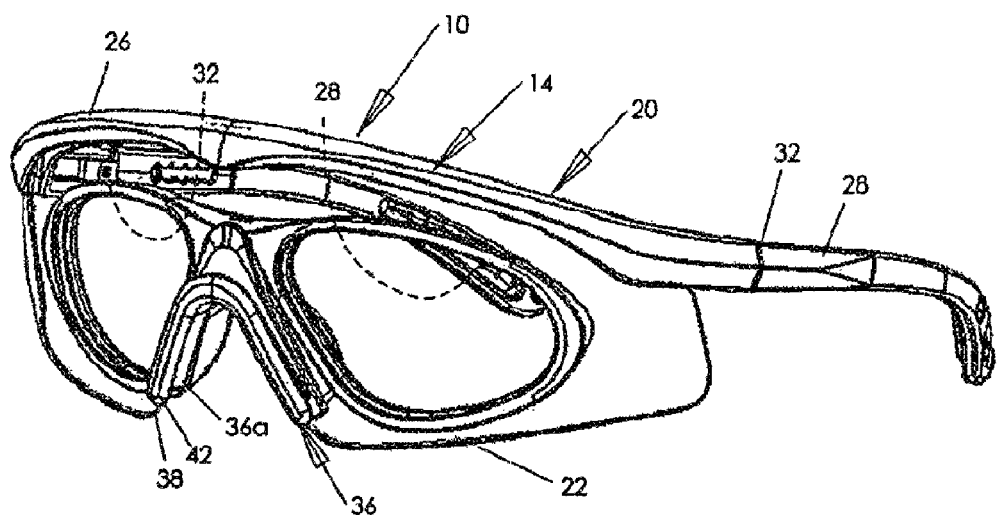
FIG. 1 is a perspective view of a first embodiment of the invention.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

This application is a divisional of U.S. Ser. No. 11/435,546 filed May 17, 2006 which claims the benefit of U.S. provisional application Ser. Nos. 60/681,610 filed May 17, 2005 and 60/722,575 filed Oct. 1, 2005, the disclosures of all three applications are herein incorporated by reference.

FIG. 1 illustrates a first assembly 10 that incorporates the present invention. The assembly 10 includes a military-type protective shield 14 such as the Sawfly™ shield available from Revision Military of Montreal, Canada, or Revision Eyewear, Ltd. of Williston, Vt., USA. The shield 14 includes a frame 20 which releasably holds a lens 22. The lens 22 can be a projectile impact resistant lens. In this regard the lens 22 can be composed of optical grade polycarbonate having a thickness of about 2.4 mm in a central location and a decreasing thickness to about 1.8 mm at its edges. The frame 20 includes a frame bar or bridge 26 and a pair of side temples 28. The temples 28 are pivotally attached to the bridge 26 by hinges 32. Provisions can be made along the temples for adjusting the length of the temples.

A nosepiece 36 is fit onto the lens 22 along a notched area 38. Provisions in the form of tabs, hooks or claws 42 are provided in the notched area 38 to underlie bottom edges 36a of the nosepiece to hold the nosepiece to the lens 22. The nosepiece 36 is snapped up into the lens 22 until the hooks 42 underlie the edges 36a.

Figure 1A:
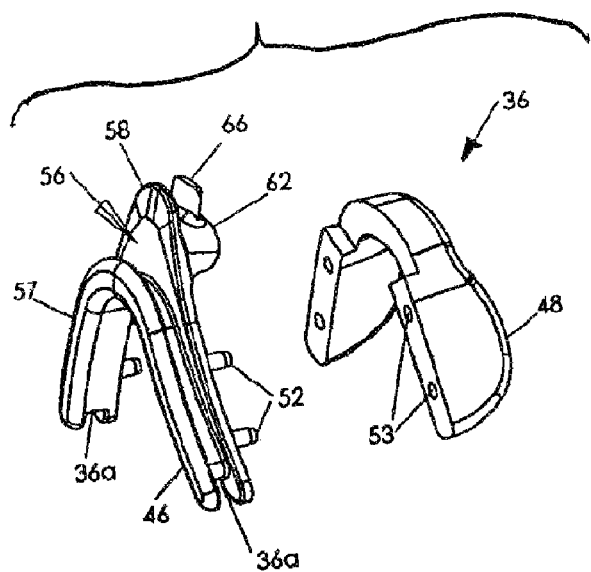
FIG. 1A is an exploded perspective view of a nosepiece taken from FIG. 1.
Figure 1C:
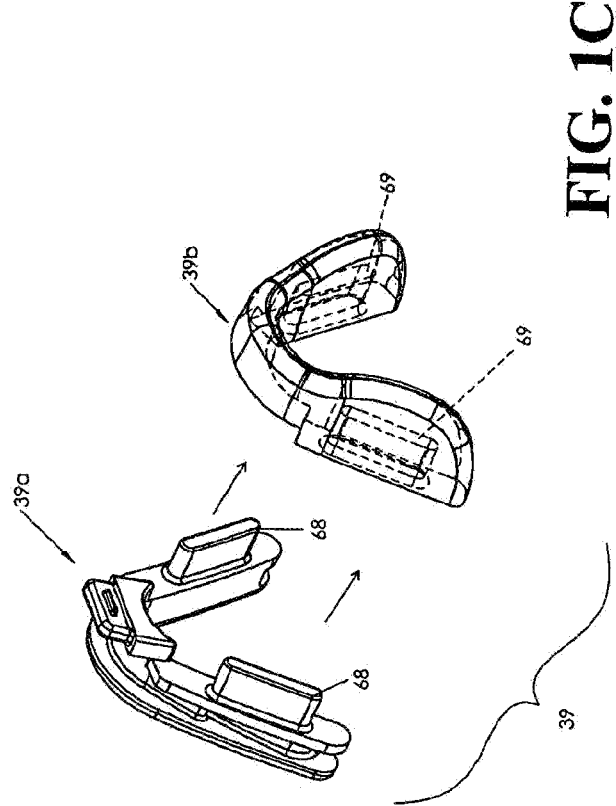
FIG. 1C is an exploded perspective view of an alternate nosepiece.
Figure 1D:
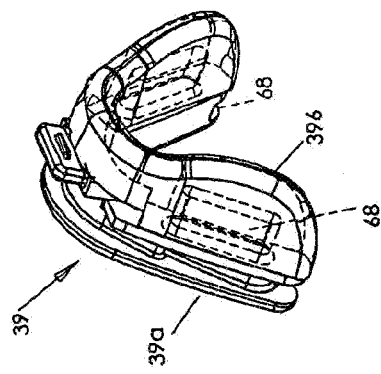
FIG. 1D is a perspective view of the alternate nosepiece of FIG. 1C, as assembled.
Figure 1B:
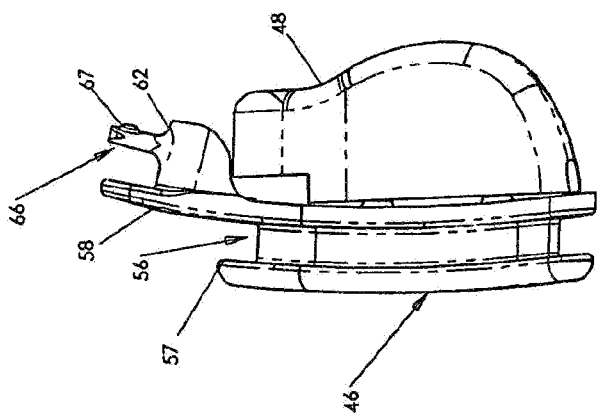
FIG. 1B is a side view of the nosepiece of FIG. 1A as assembled.

As illustrated in FIGS. 1A and 1B the nosepiece 36 comprises a two-part assembly. A front base part 46 locks to a rear cushion part 48 via locking pins 52 that are secured into apertures 53. Preferably, adhesive is applied to the pins 52 before assembly into the apertures 53 for a secure adhesive fixation of the two-part assembly. The rear cushion part can be a soft rubber part. The front base part 46 includes a groove 56 for receiving the notched area 38 of the lens 22, the groove in part defined by a front wall 57 and a rear wall 58. A rearward directed abutment 62 extends from the rear wall 58 which serves to vertically support an inner lens sub-assembly 65 as described below. A retaining tab 66 extends vertically from the abutment 62. The retaining tab 66 includes a rearward directed locking nub 67.

The front base part 46 is preferably composed of a polycarbonate material and the rear cushion part 48 is preferably composed of a relatively soft PVC material.

FIGS. 1C and 1D illustrate an alternate embodiment nosepiece 39 having a front base part 39a and a rear cushion part 39b. The front base part 39a includes tabular flanges 68 that are configured to be closely fit into rectangular holes 69 that are formed in the rear cushion part 39b. Preferably, adhesive is applied to the tabular flanges 68 before insertion into the holes 69 to ensure a tight fixation of the two parts 39a/39b.

Figure 2:
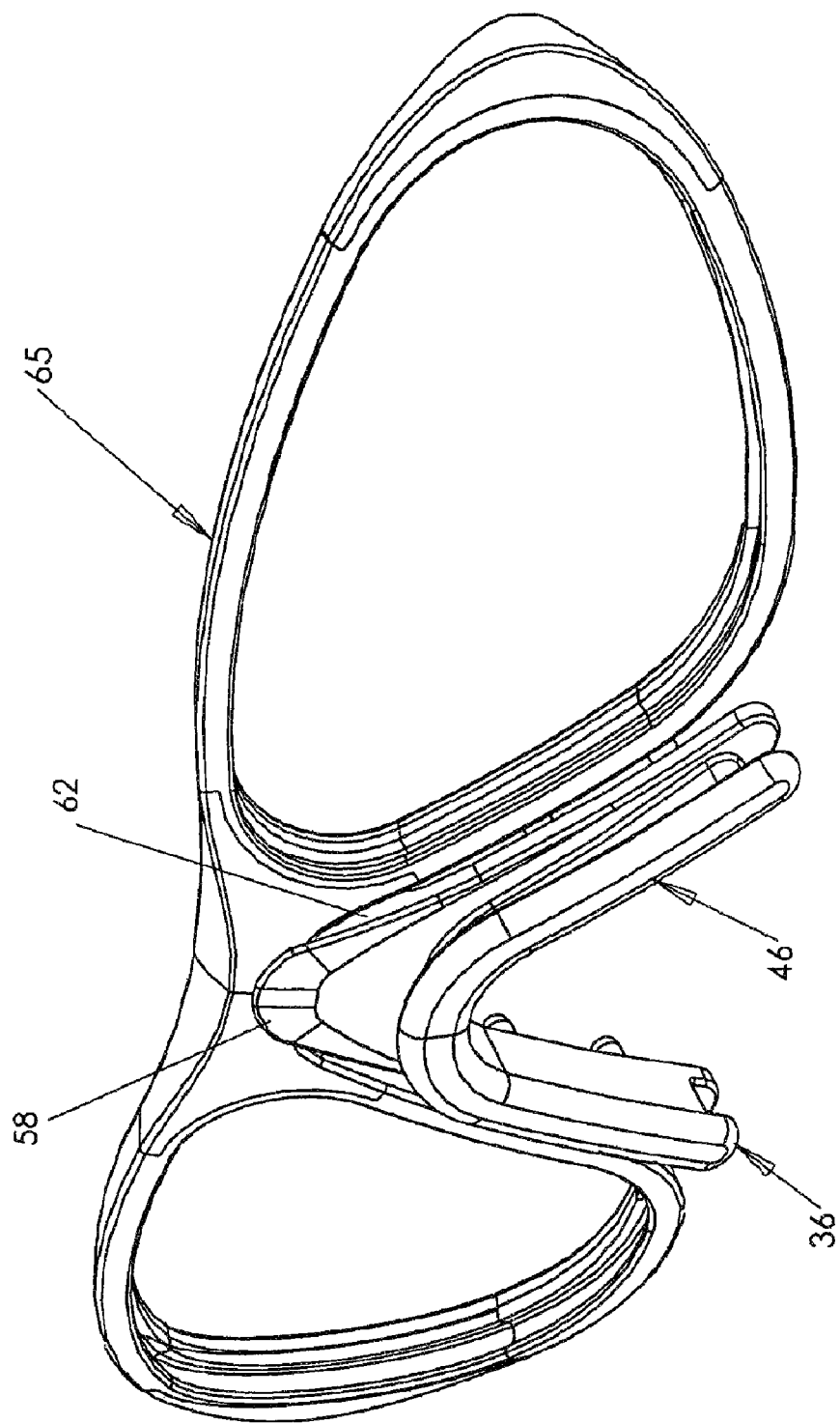
FIG. 2 is a perspective view of a portion of embodiment shown in FIG. 1.

As illustrated in FIG. 2, the inner lens sub-assembly 65 is fit onto the abutment 62 behind the rear wall 58 of the groove and onto the retaining tab 66. The inner lens sub-assembly 65 includes an aperture described below which captures the tab 66 to lock assembly 65 to the base part 46.

As illustrated in FIGS. 3-6B, the inner lens sub-assembly 65 comprises a frame 72 that holds left and right lenses 76, 78. The frame 72 comprises a base frame part 82 that includes left and right apertured parts 84, 85 that respectively surround and hold the lenses 76, 78, and a bridge part 86 that connects the apertured parts 84, 85. The base frame part 82 is preferably composed of a relatively hard polycarbonate material. The base frame part 82 provides a rigid skeletal structure for supporting and orienting the lenses 76, 78. The lenses 76, 78 are preferably vision-correcting, prescription lenses or other type of vision enhancing or protecting lenses. The lenses 76, 78 can advantageously be composed of a polycarbonate prescription lens material or a CR39 plastic polymer prescription lens material.

A second frame part is 102 is applied onto the base frame part 82. The second frame part 102 includes end extending portions 106, 108 that are located at the opposite lateral extremes of the frame 72. When assembled, the portions 106, 108 extend forwardly of the adjacent regions 84, 85 and act as soft bumpers between the frame 72 and the lens 22. The second frame part 102 also extends behind the frame 72 with a surface backing portion 112 substantially laterally co-extensive with the apertured parts 84, 85 and bridge 86 and continuous with the extending portions 106, 108.

The second frame part 102 is preferably composed of a PVC material or a urethane material that is softer than the material of the first frame part 82. The material of the second frame part is resilient and more grippable than the material of the first frame part 82. Being softer than the first frame part 82, the material of the second frame part 102 is more shatter resistant from projectiles and force contact and would tend to retain together pieces of an otherwise shattered frame part 82.

The softer material of the frame part 102 also prevents scratching of the lens 22 by the frame 72 during incidental contact during assembly of the inner lens sub-assembly 65 to the shield 14. The extending portions 106, 108 also act as spacers between the frame 72 and the lens 22 to ensure air flow between the lens 22 and the lenses 76, 78 to reduce fogging.

Preferably, the second frame part 102 is "overmolded" onto the first frame part 82. According to this method, after the first frame part 82 is molded, it is placed into a second mold, or the first mold can be made adjustable to increase in size and change in shape, and the second frame part 102 is then molded onto the first frame part 82. Example of overmolding methods for other articles are described in U.S. Pat. Nos. 6,601,272 B2; 5,182,0321 and 5,934,762 all herein incorporated by reference.

Figure 4:
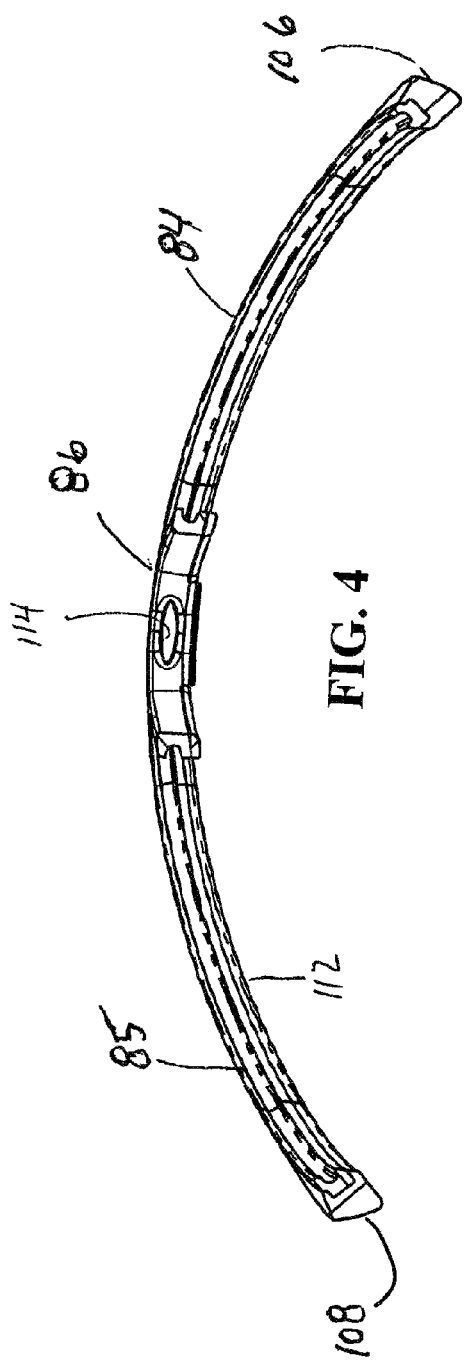
FIG. 4 is a sectional view taken generally along line 4-4 of FIG. 3.
Figure 3:
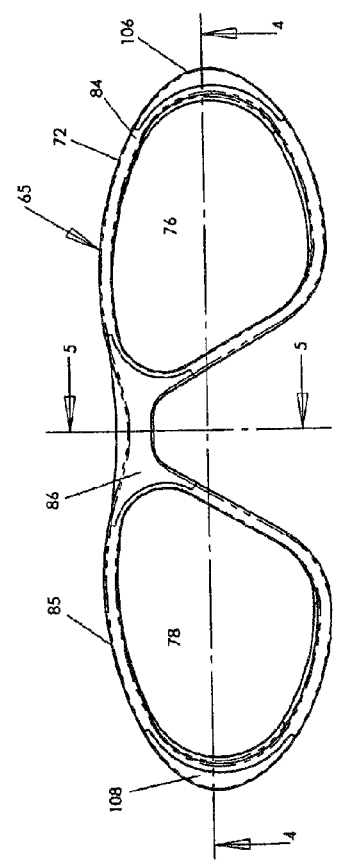
FIG. 3 is a front view of a prescription lens frame taken from FIG. 1.
Figure 5:
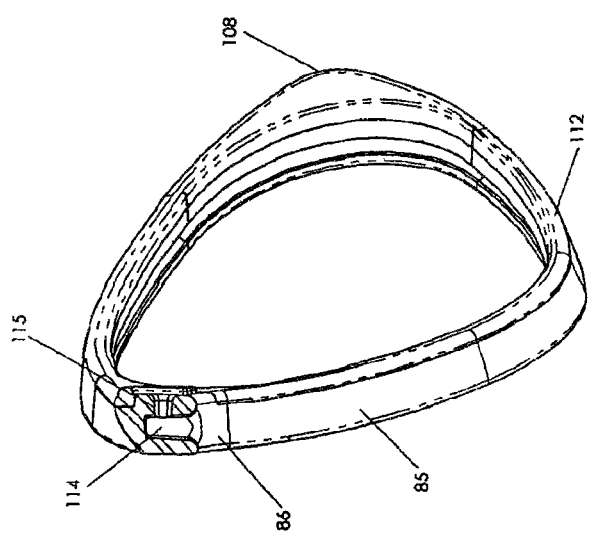
FIG. 5 is a sectional view taken generally along 5-5 of FIG. 3.

FIGS. 4 and 5 illustrate that the bridge 86 includes an oval aperture 114 intersected by a lock aperture 115 at approximately a right angle. When the inner lens sub-assembly 65 is fit onto the abutment 62 the tab 66 fits into the oval aperture 115 until the nub 67 snaps into the lock aperture 115, to releasably lock the assembly 65 to the nosepiece 36.

Figure 6A:
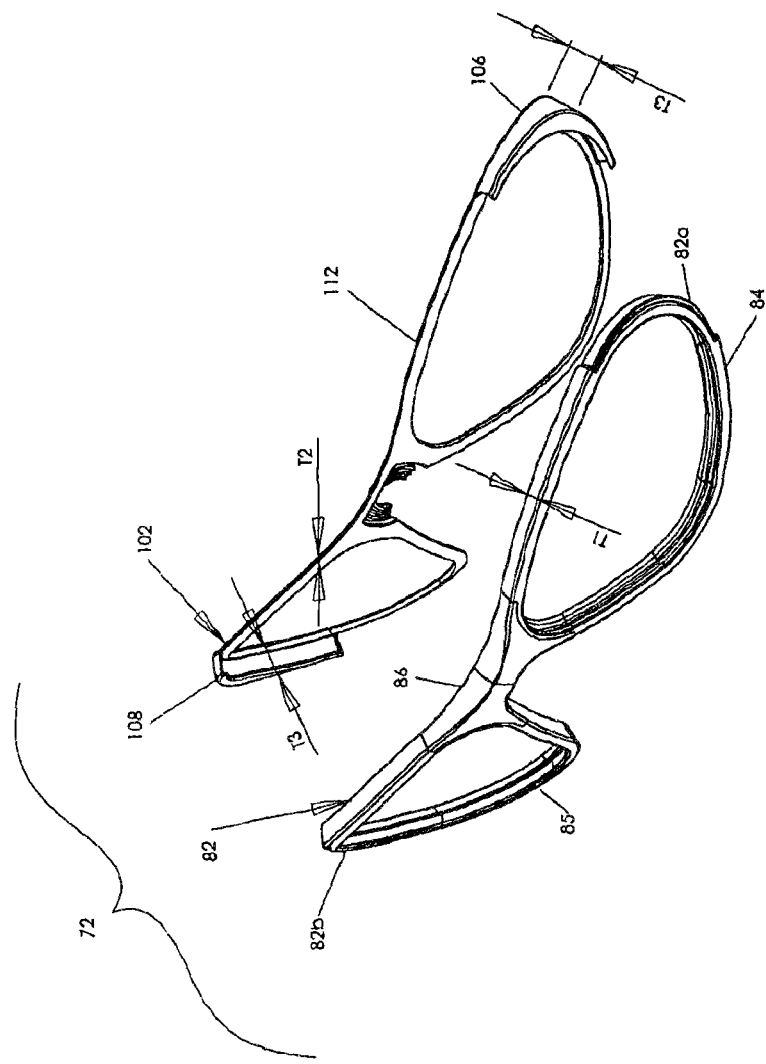
FIG. 6A is an exploded front perspective view of the lens frame of FIG. 3.
Figure 6B:
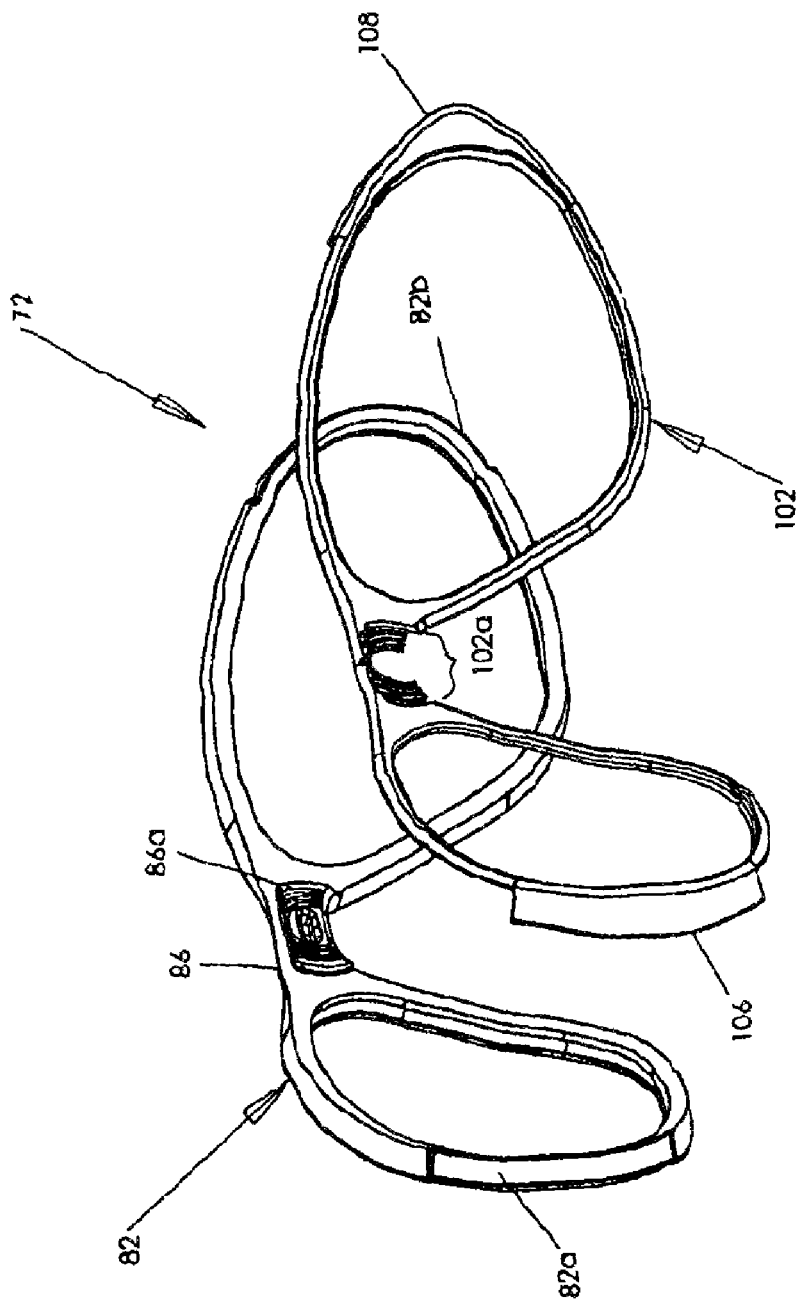
FIG. 6B is an exploded rear perspective view of the lens frame of FIG. 3.

FIGS. 6A and 6B illustrate the frame 72 comprising the first frame portion 82 and the overmolded second frame portion 102 as separated components to illustrate more clearly the relative shapes of these two components. The frame portion 82 includes indented lateral regions 82a, 82b around which the portions 106, 108 are molded. As shown in FIG. 6B, the bridge portion 86 includes a series of curved grooves 86a into which a series of curved ribs 102a of the second frame portion 102 are molded. The ribs 102a provide a frictional gripping region for the user to grasp the frame 72 to fit the assembly 65 onto the shield 14. As illustrated in FIG. 6A, the first frame portion has a thickness t1, preferably about 4 mm. The second frame portion 102 has a thickness t2 throughout the portion 112, preferably about 1 mm. The end portions 106, 108 have a thickness t3, preferably about 5 mm.

Figure 7:
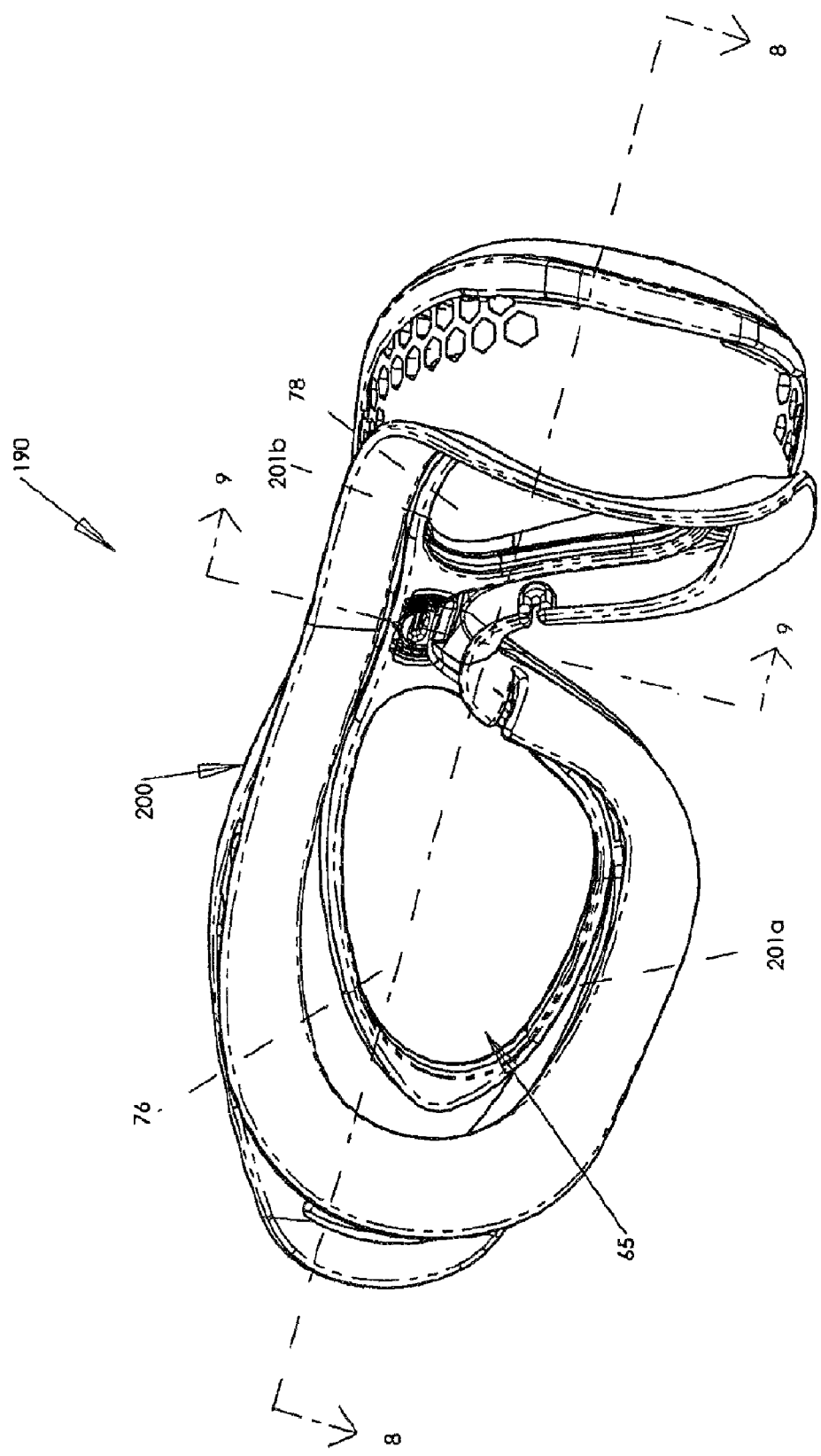
FIG. 7 is a perspective view of a second embodiment of the invention.
Figure 8:
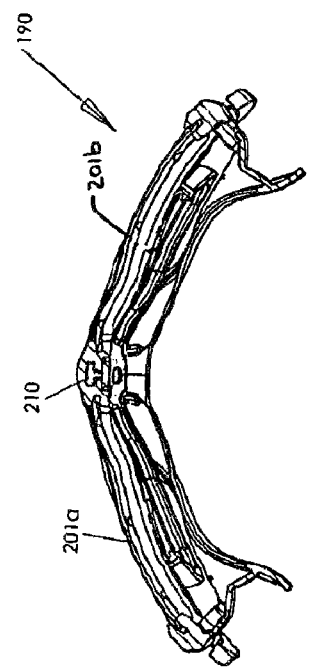
FIG. 8 is a sectional view taken generally along line 8-8 of FIG. 7.
Figure 9:
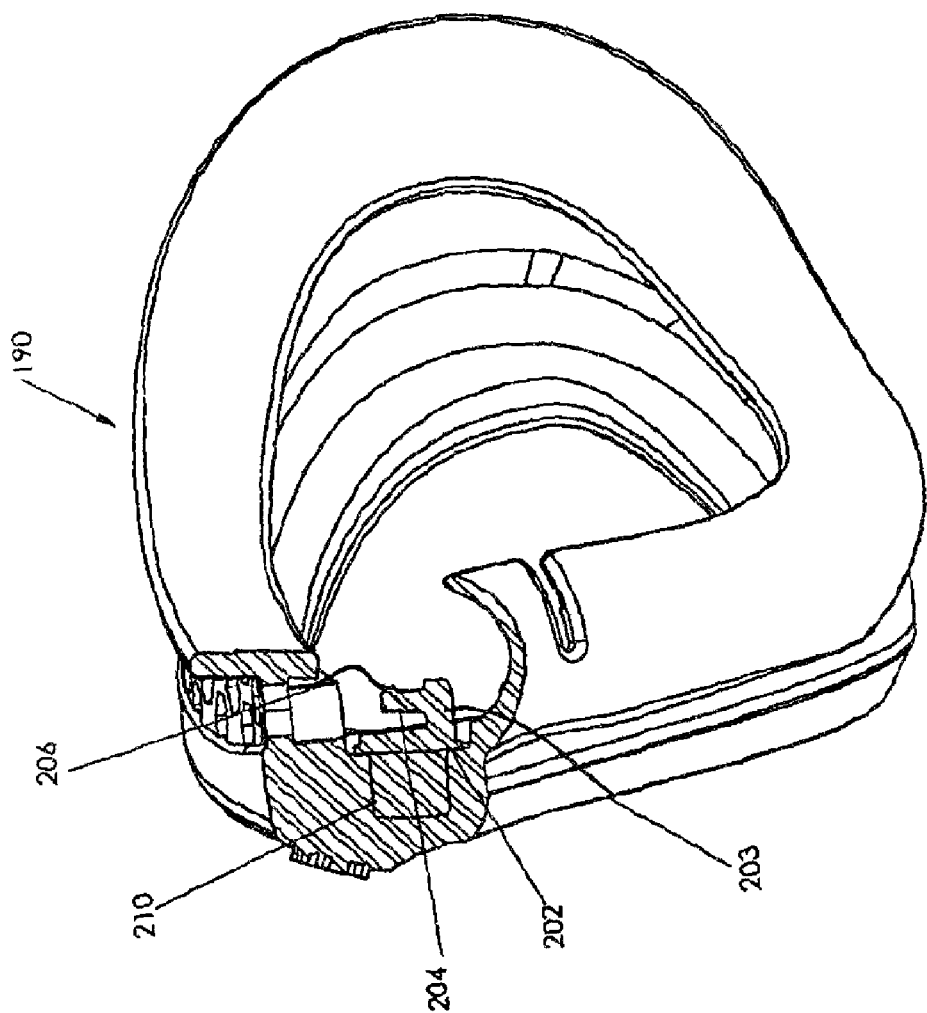
FIG. 9 is a sectional view taken generally along line 9-9 of FIG. 7.

FIGS. 7-9 illustrate an alternate embodiment 190 wherein the previously described inner lens sub-assembly 65 can be fit into goggles 200 that enclose the user's eyes on the user's face. The goggles offer sunlight, wind, dust and debris protection. The goggles can be Bullet Ant™ military-type goggles available from Revision Military of Montreal, Canada, or Revision Eyewear, Ltd. of Williston, Vt., USA. The goggles 200 can include left and right lenses 201a, 201b that can be projective impact resistant. In this regard the lens 201a, 201b can be composed of optical grade polycarbonate having a thickness of about 2.2 mm in a center of the lens and about 1.8 to 1.9 mm at the edge. In this regard, FIG. 9 illustrates that the goggles 200 include a support 202 that includes an abutment 203, a tab 204 extending perpendicularly from the abutment with a nub 206 extending perpendicularly from the tab 204. The support 202 includes an anchor portion 210 that is locked into surrounding portions of the goggle 200. The parts 203, 204 and 206 function identically to the parts 62, 66 and 67 of the previously described embodiment. The support is preferably composed of a polyamide or Nylon material.

As with the previously described embodiment, the frame part 102 provided on the frame part 82 prevents scratching of lenses 201a, 201b of the goggles 200 and will space the frame 72 and lenses 76, 78 from a rear surface of the lenses 201a, 201b to ensure an air space therebetween to reduce fogging. The previously stated handling and shatter resistance advantageous of the sub-assembly 65 is applicable to the second embodiment as well.

The subassembly 65 can be used with either the shield 14 or the goggles 200, providing a universal part.

Figure 7A:
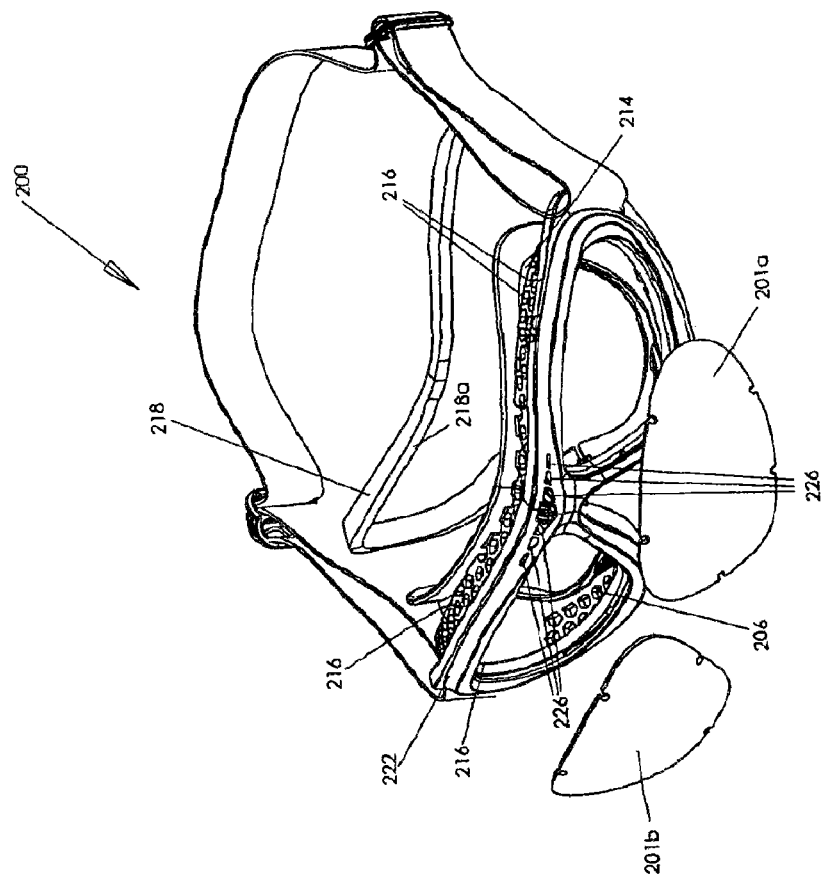
FIG. 7A is an exploded perspective view of the embodiment of FIG. 7 with auxiliary frame not shown.

FIG. 7A illustrates some features of the goggles 200, with the auxiliary frame not shown. The goggles 200 include a surrounding flexible skirt 214 that includes a plurality of hexagonal vent holes 216 through the top and bottom. An air permeable filter material ring 218 is fit into the skirt 214 and substantially covers the inside of the holes 214. The front frame 222 of the goggles includes a plurality of frontal vent holes 226 that allow outside air to enter into the goggles through a front face of the ring 218.

Figure 10:
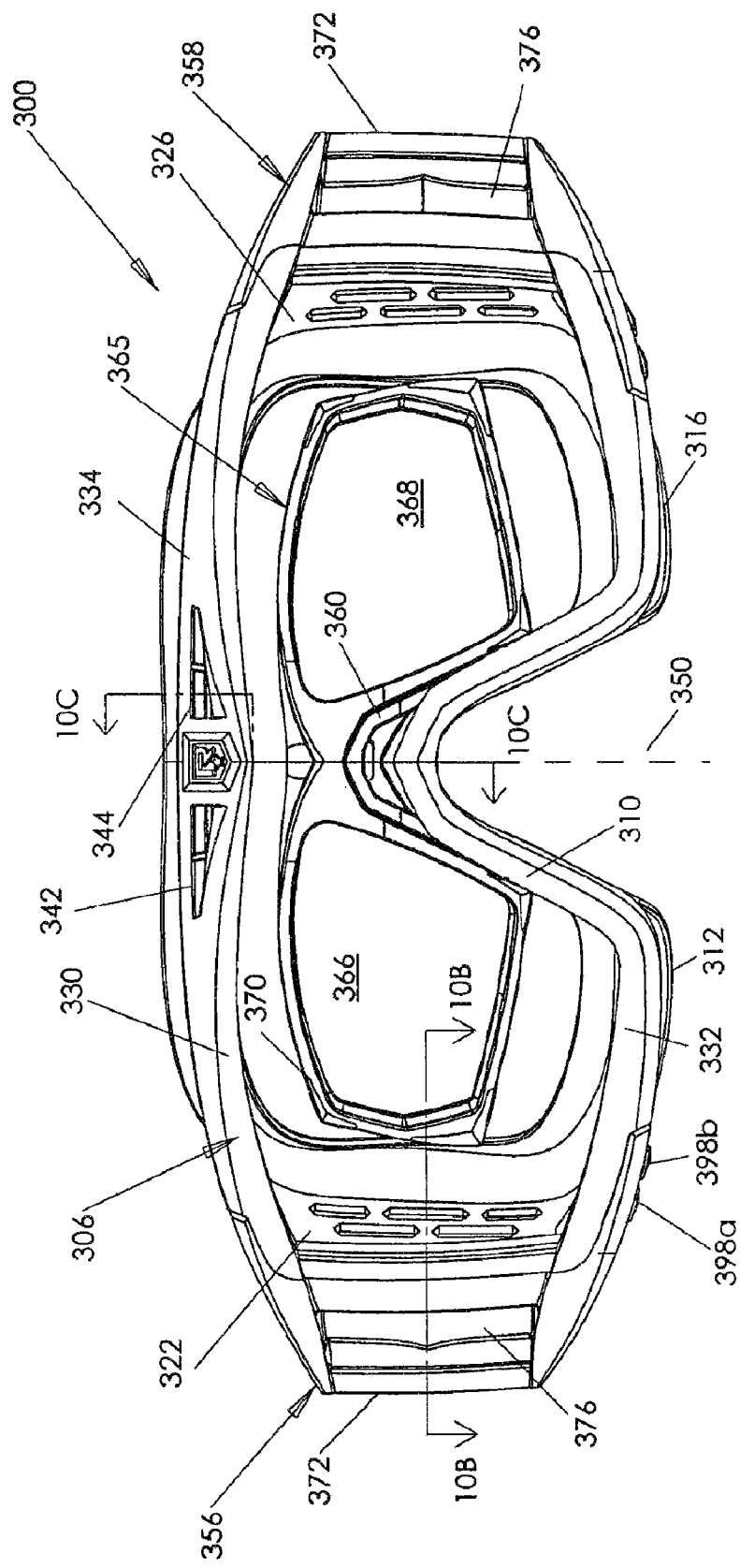
FIG. 10 is a front view of a pair of goggles according to another aspect of the invention.

FIG. 10 illustrates an alternate embodiment protective eyewear in the form of goggles 300. The goggles offer sunlight, wind, dust and debris protection. The goggles can be Desert Locust™ goggles available from Revision Military of Montreal, Canada, or Revision Eyewear, Ltd. of Williston, Vt., USA.

Figure 10A:
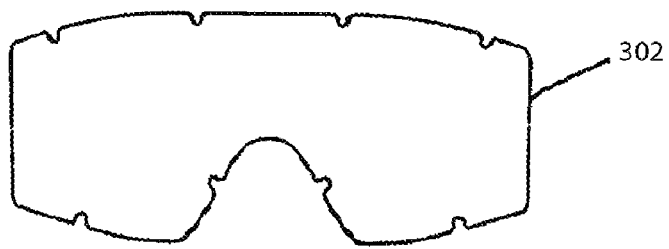
FIG. 10A is a front view of a lens taken from the embodiment shown in FIG. 10.

The goggles 300 are mirror image identical across a centerline 350, so that a description of one side is sufficient to describe both sides. The goggles 300 include a front protective lens 302 (FIG. 10A) that is removably held within a frame 306. The protective lens can be clear or a light treating or blocking lens, or other type of lens. The lens can be a projectile impact resistant lens. The lens can be composed of optical grade polycarbonate having a thickness of about 3 mm in a center of the lens and about 2.1 mm at the edge. The frame 306 includes a concave nose conforming region 310, bottom wall regions 312, 316, sidewall regions 322, 326, an upper front region 330, a lower front region 332, and a top wall region 334. The upper front region 330 includes two vent openings 342, 344 that straddle a centerline 350 of the frame 306, close to the centerline 350.

One strap anchor 356, 358 is mounted on each side of the frame 306. Each strap anchor 356, 358 is removably mounted to the frame 306 as described below. The top wall region 334, the bottom wall regions, 312, 316 and the sidewalls regions 322, 326 all include ventilation openings generally indicated as 357. An filter material 358 (shown only and FIGS. 10B and 10C) is applied over the ventilation openings.

The goggles 300 include an adapter 360 that snap engages to an inside of the nose conforming region 310. A lens subassembly 365 is provided, held behind the protective lens 302. The subassembly includes at least one, and preferably two auxiliary lenses 366, 368, carried by an auxiliary frame 370. The lenses can be prescription lenses, protective lenses, light treating lenses, or any other type of known lenses. The auxiliary frame 370 snap engages to the adapter 360.

Figure 11:
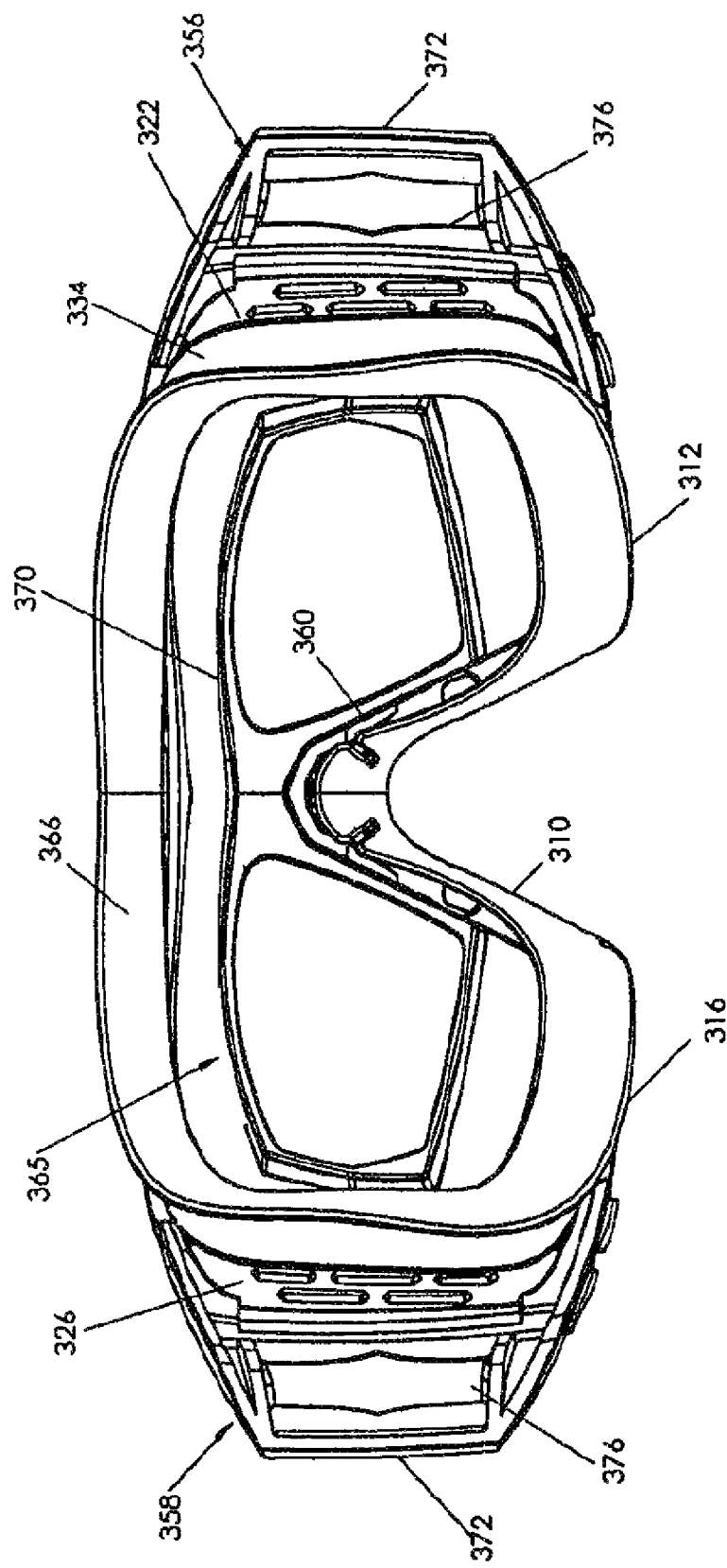
FIG. 11 is a rear view of the goggles of FIG. 10.
Figure 12:
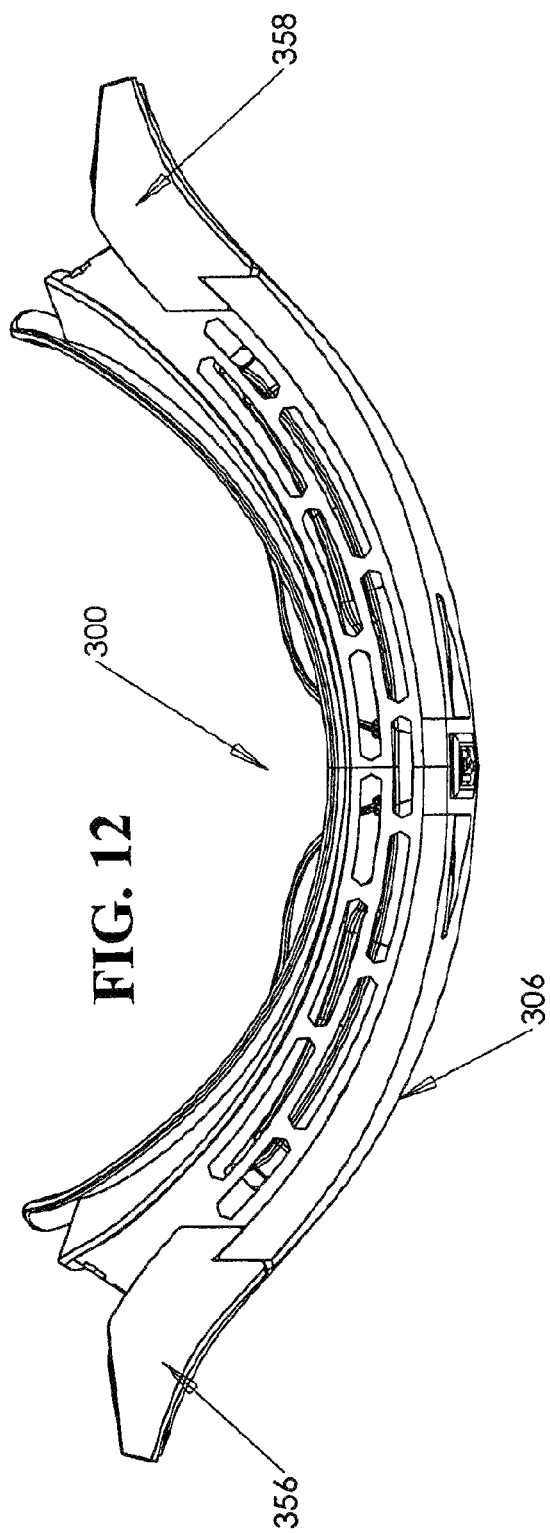
FIG. 12 is a top view of the goggles of FIG. 10.
Figure 13:
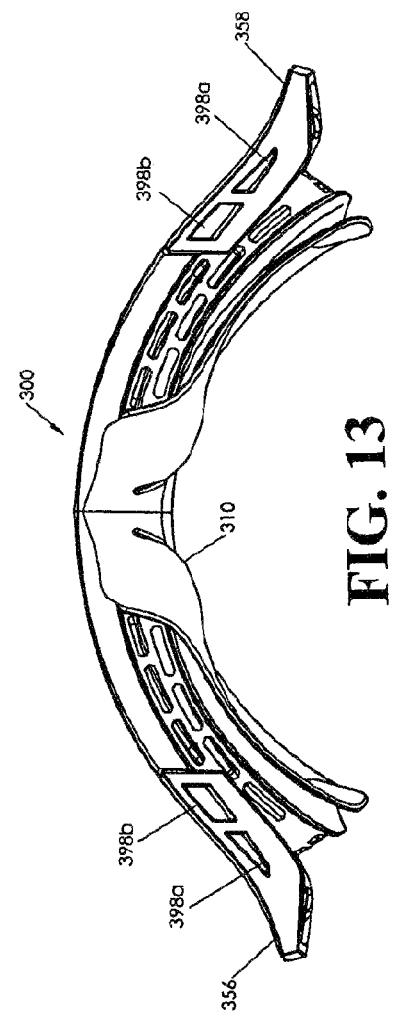
FIG. 13 is a bottom view of the goggles of FIG. 10.
Figure 15:
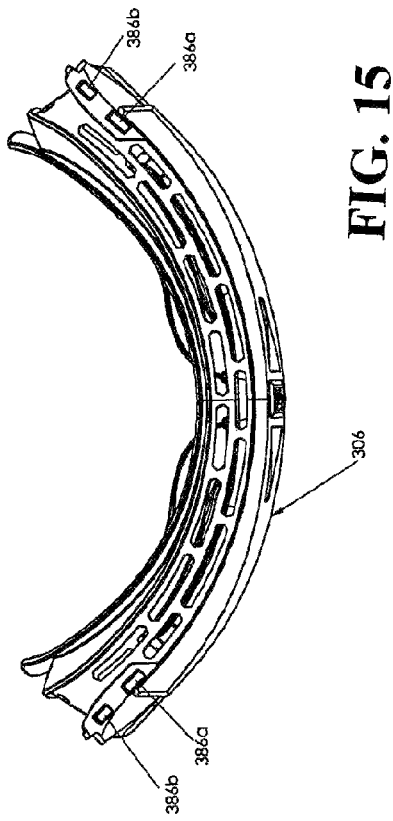
FIG. 15 is a top view of a portion of the goggles shown in FIG. 10.
Figure 14:
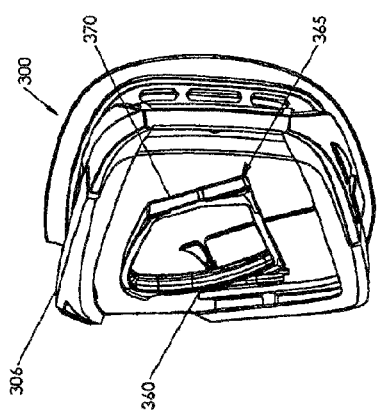
FIG. 14 is a right side view of the goggles of FIG. 10.
Figure 17:
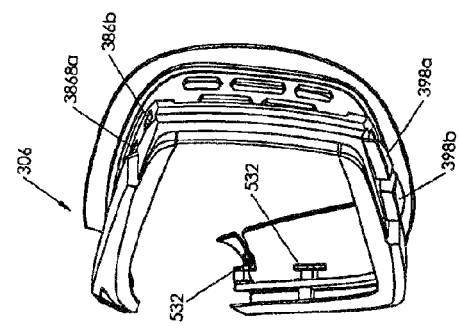
FIG. 17 is a right side view of the portion shown in FIG. 15.
Figure 16:
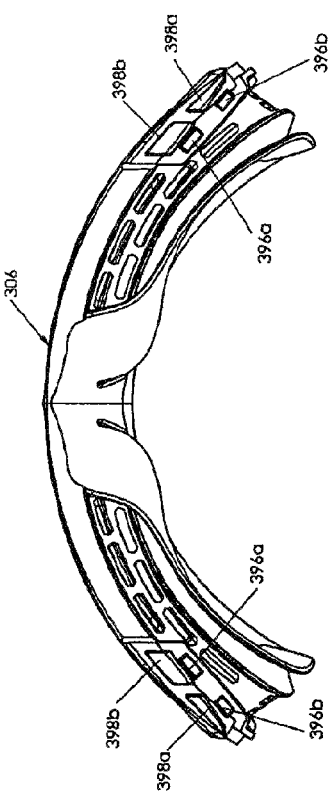
FIG. 16 is a bottom view of the portion shown in FIG. 15.

FIG. 11 illustrates that the goggles 300 include a rear skirt or surrounding flexible flange 366 that is formed continuously with the portions 310, 312, 316, 322, 326, 334. The flange 366 conforms comfortably to the user's face as the goggles are worn.

The strap anchors 356, 358 each include an outer strap-engaging bar 372 and an air louver 376. The air louver 376 is angled toward the respective sidewall region 322, 326 to direct air toward the ventilation openings through sidewall regions and into the interior of the goggle.

Referring to FIGS. 15-18E, the strap anchors 356, 358 are mounted to the frame 306 by two top, downwardly extended rectangular tabs 382a, 382b, extending from a top flange 383 of the strap anchor, that fit tightly into oblong or rectangular holes 386a, 386b in the top wall region 334, and bottom, upwardly extended rectangular tabs 392a, 392b extending from a bottom flange 393 of the strap anchor, that fits tightly into oblong or rectangular holes 396a, 396b in the respective bottom wall region 312, 316. Additionally, the bottom flange 393 of the anchor includes a plurality, such as two, openings 396a, 396b that register with grip tabs, or grip bumps or grip warts 398a, 398b that have a height greater than the thickness of the bottom flange 393 such that the grip warts are exposed outwardly of the bottom flange 393 of the strap anchor. The grip warts 398a, 398b provide an increased gripping or friction between the goggles and the user's fingers for manipulating the goggle on the user's face. This is advantageous particularly if the user is wearing gloves.

Preferably, the frame 306 is composed of a relatively soft urethane material, and the strap anchors 356, 358 are composed of a harder nylon material forming rigid parts.

When the strap anchors 356, 358 are assembled to the frame 306, preferably the lens 302 is not yet fit into the frame 306. The tabs 382a, 382b and 392a, 392b are fit into their respective holes 386a, 386b and 396a, 396b in the frame 306. When the lens is installed, it rigidifies the frame 306 and thus helps to ensure the reliable engagement of the tabs and holes to secure the strap anchors 356, 358 to the frame 306.

Figure 10B:
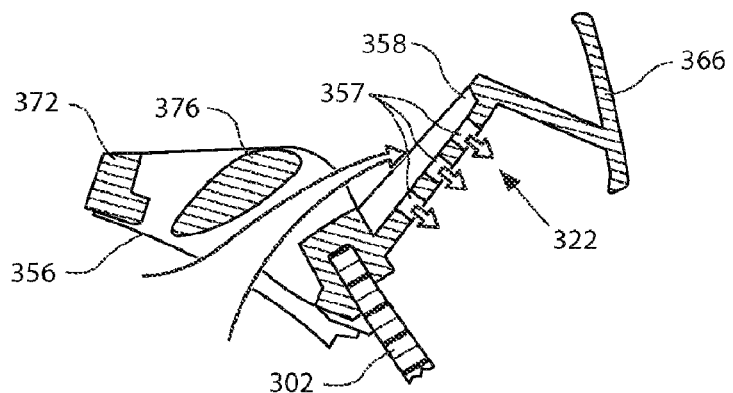
FIG. 10B is a sectional view taken generally along line 10B-10B of FIG. 10.

Referring to FIG. 10B, air can be inducted or pass through the filter material 358 that covers the ventilation openings 357 of the sidewall regions, 322, 326 directed by the louvers 376 that are angled inwardly.

Figure 10C:
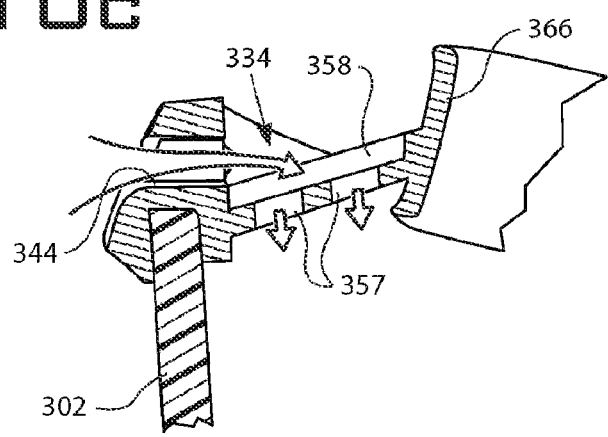
FIG. 10C is a sectional view taken generally along line 10C-10C of FIG. 10.

Referring to FIG. 10C, the front vents 342, 344 provide an air flow path from in front of the goggles to an open area above the ventilation openings through the top wall region 334. Air can be inducted or pass through the vents 342, 344 to above the filter material of 358 that covers the ventilation openings 357 of the top wall region 334.

Figure 19:
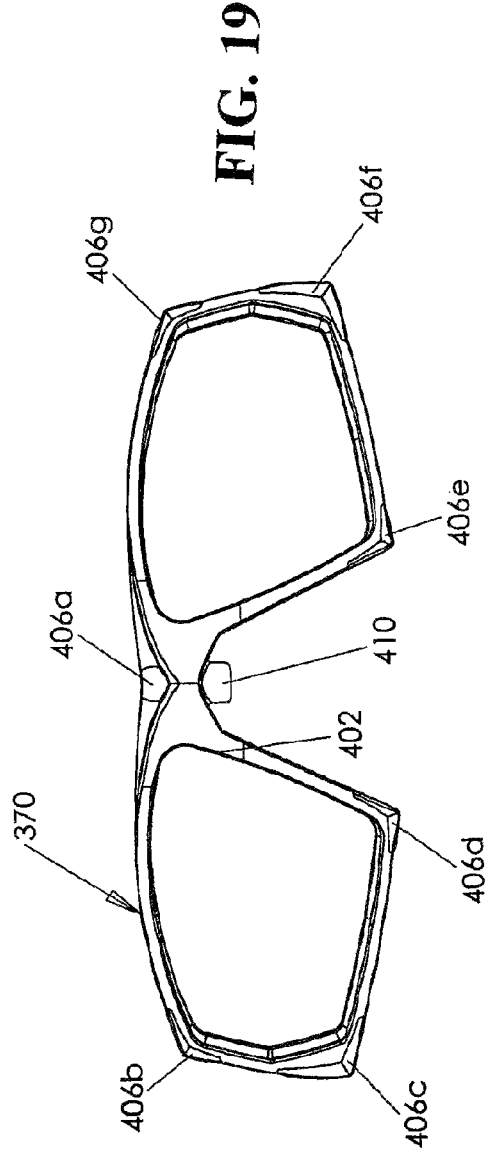
FIG. 19 is a front view of an auxiliary frame taken from FIG. 10.
Figure 20:
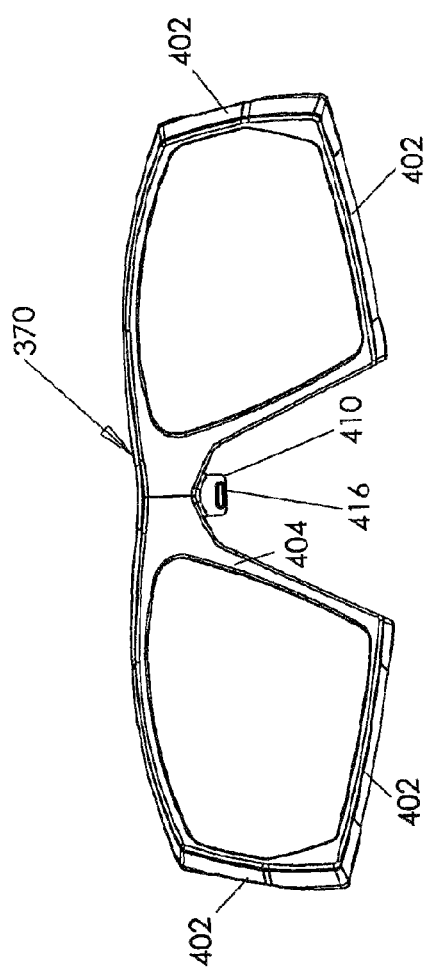
FIG. 20 is a rear view of the auxiliary shown in FIG. 19.
Figure 21:
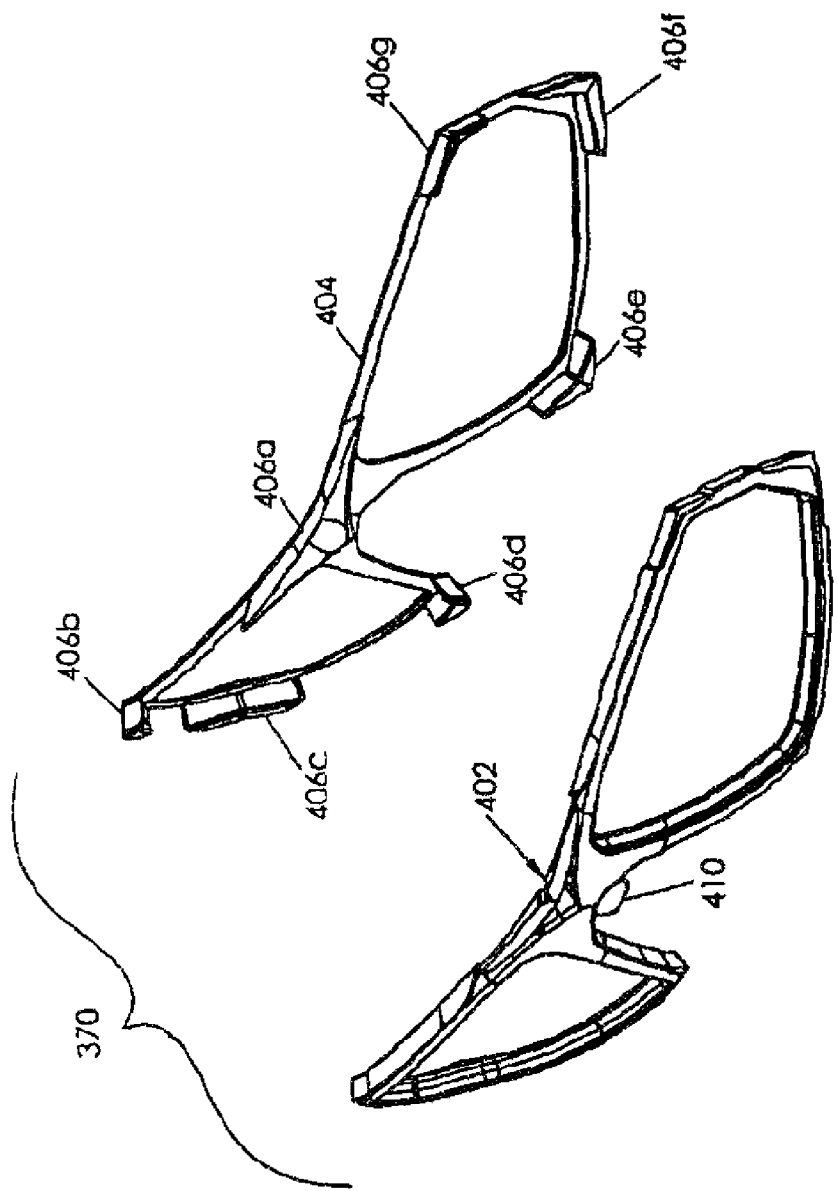
FIG. 21 is an exploded perspective view of the auxiliary shown in FIG. 19.
Figure 22:
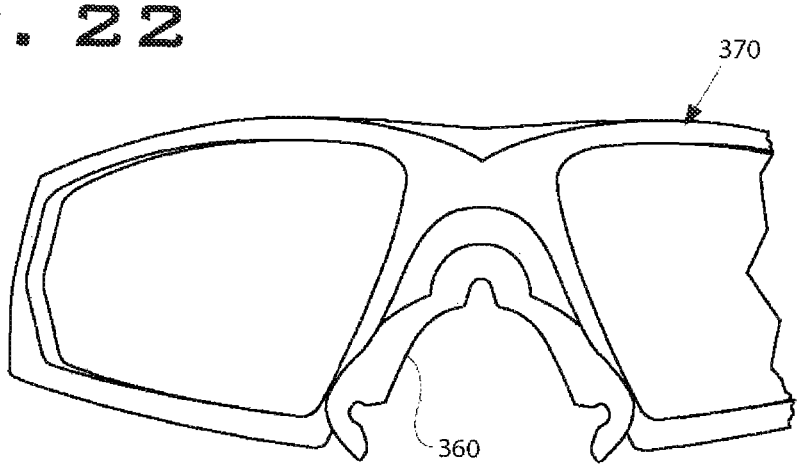
FIG. 22 is a fragmentary front view of the auxiliary frame mounted to an adapter taken from FIG. 10.
Figure 23:
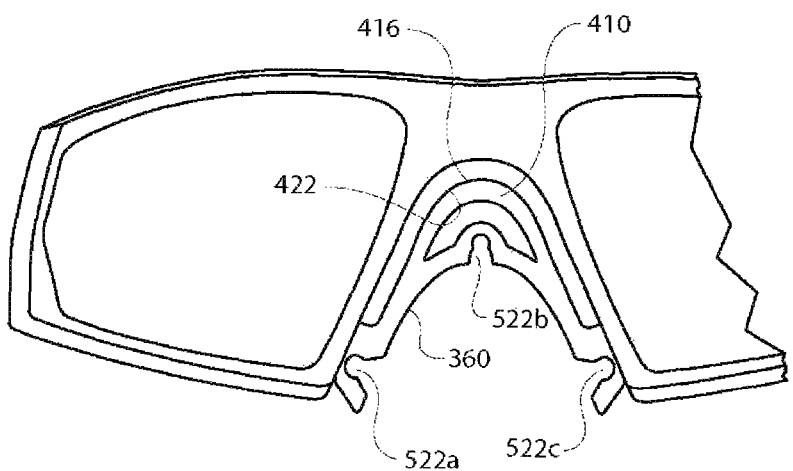
FIG. 23 is a fragmentary rear view of the prescription lens frame mounted to an adapter shown in FIG. 22.
Figure 24:
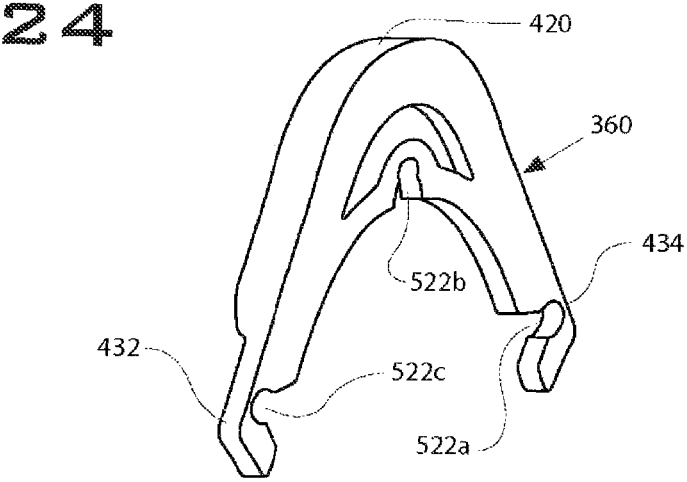
FIG. 24 is a perspective view of the adapter shown in FIG. 22.

The auxiliary frame 370 is illustrated in FIGS. 19-21. The auxiliary frame 370 includes a hard base frame part 402 that is over molded completely on a backside face by a second frame part 404 that extends around the hard frame 402 to the front side in regions 406a, 406b, 406c, 406d, 406e, 406f and 406g. The hard frame part 402 and the soft over molded second frame part 404 are substantially similar in structure, method of manufacturing, materials of construction, thickness, function and advantages as the configuration described above with respect to FIG. 6A and FIG. 6B, regarding the frame parts 82, 102. For example, the soft regions 406a, 406b, 406c, 406d, 406e, 406f and 406g extend slightly forwardly of the hard frame part 402 and help to prevent scratching of the protective lens by the hard frame part 402, and also help separate the protective lens from the auxiliary lens to allow air flow therebetween to help prevent fogging of the protective lens.

FIGS. 6A, 6B and 21 illustrate two embodiments of the auxiliary frame 15 in exploded fashion, with the hard base frame part and the soft second frame part shown as separate elements for clarity of description. In practice, the two parts are not necessarily separable since preferably the soft layer component is molded onto the hard frame component.

A downwardly extended tab 410 is used to secure the auxiliary frame 370 to the adapter 360. The tab 410 includes a locking tang, ledge or pin 416 that extends horizontally. The adapter 360 includes a slot 420 for receiving the tab 410 and a recess ledge 422 for receiving the locking tang 416. When the auxiliary frame 370 is pressed down onto the concave, nose conforming region 310, inside the goggle frame 306, the tab 410 slides within the slot 420 and the tang 416 snap engages beneath the recess ledge 422 and removably secures the auxiliary frame 370 to the protective frame 306. To assist in installing the auxiliary frame 370 onto the concave region 410, guide portions 432, 434 could be provided on the adapter 360.

The adapter 360 includes a mounting flange 520 that includes three resilient snap slots 522a, 522b, 522c. Each snap slot engages a corresponding pin 532 formed inside and as part of the protective frame 306 (only two pins shown in FIG. 17). This forms a three-point, removable attachment of the adapter 360 to the protective frame 306.

Figure 25:
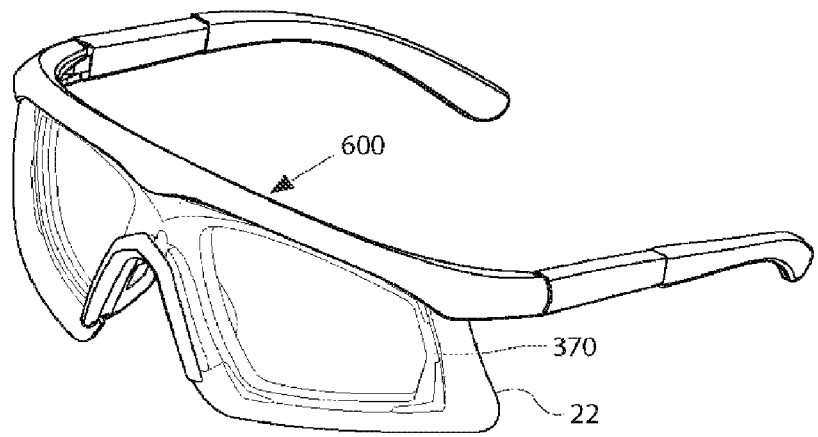
FIG. 25 is a perspective view of a further embodiment of the invention.
Figure 26:
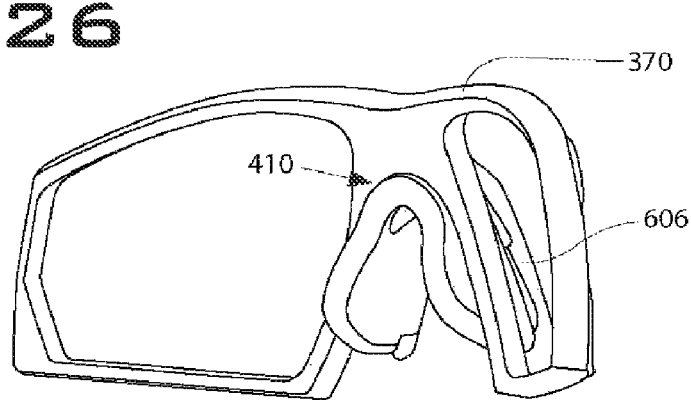
FIG. 26 is a rear perspective view of an auxiliary frame and an alternate nosepiece taken from FIG. 25.
Figure 27:
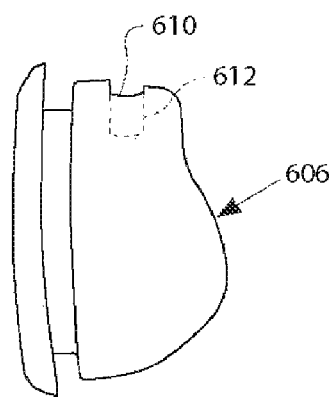
FIG. 27 is a right side view of the alternate nosepiece taken from FIG. 25.

FIG. 25 shows a protective shield 600 similar to the protective shield shown in FIG. 1. However, the auxiliary frame 370 described in FIGS. 19-21 snap fits into an alternate nosepiece 606 (FIGS. 26, 27). The alternate nosepiece 606 installs onto the lens 22 in the same fashion as described with respect to FIG. 1, however the alternate nosepiece 606 includes a slot 610 (shown with hidden line in FIG. 27) having a recess ledge 612. The tab 410 slides into the slot 610 and the tang 416 snap beneath the recess ledge 612 to removably retain the auxiliary lens 370 onto the alternate nosepiece 606.

Figure 28:
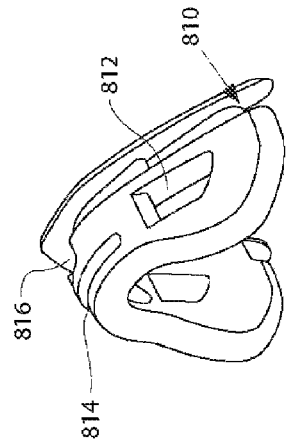
FIG. 28 is a fragmentary perspective view of an alternate embodiment auxiliary frame and nose piece.

FIG. 28 shows an alternate embodiment auxiliary frame 670 that is substantially identical to the auxiliary frame 370 except that raised ribs 686, 688 are formed on side walls 672, 674 of lens frames 678, 680, below the bridge 684. The ribs 686, 688 extend substantially vertically from a position near the tab 410 to a position near a bottom of the lens frames 678, 680. The ribs 686, 688 are mirror image identical across a vertical centerline of the frame 670.

An alternate nosepiece 700 for fitment to a protective shield, such as shown in FIG. 25, includes grooves 706, 708 (708 not visible) that receive the ribs 686, 688 as the frame 670 is slid down onto the nosepiece 700, until the tab 410 and the tang 416 (not shown) engage the nosepiece as previously described.

Although a nosepiece 700 is described and shown in FIG. 28, the grooves 706, 708 could also be provided in an adapter for fitment to a goggle such as shown in FIGS. 14 and 22-24.

Figure 31:
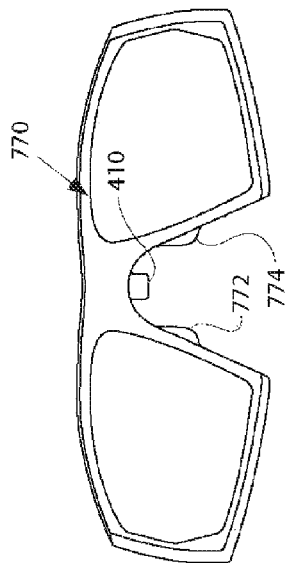
FIG. 31 is a rear perspective view of the auxiliary frame shown in FIG. 29.
Figure 29:
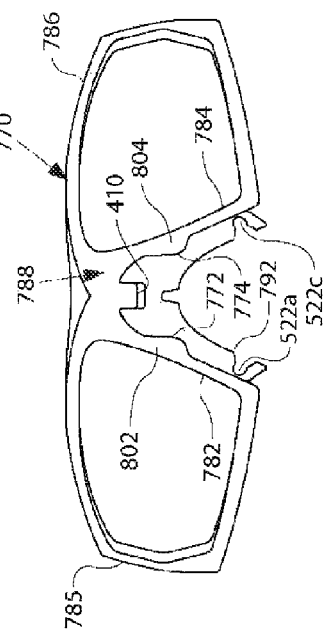
FIG. 29 is a front view of a further alternate embodiment auxiliary frame and goggle adapter.

FIGS. 29 and 31 illustrate a further embodiment auxiliary frame 770 identical to the auxiliary frame 370 except for the addition of protrusions 772, 774 arranged on the inside walls 782, 784 of the lens frames 785, 786, below the bridge 788.

The protrusions 772, 774 fit within a modified adapter 792 for mounting the auxiliary frame 770 to a goggle such as shown in FIGS. 14 and 22-24. The modified adapter 792 includes indentations 802, 804 for receiving the protrusions 772, 774. The interaction of the protrusions 772, 774 with the indentations 802, 804 can be a snap fit engagement or merely a guided arrangement. The indentations can be open in the fore and aft direction, or can be closed in the fore and aft direction. In the latter case, the indentations would guide the frame 770 in the fore and aft direction and the left and right direction. In either case, the indentations could restrain the auxiliary frame in the vertical direction as well if the interaction between the protrusions 772, 774 and the indentations 802, 804 is a snap fit engagement.

Figure 30:
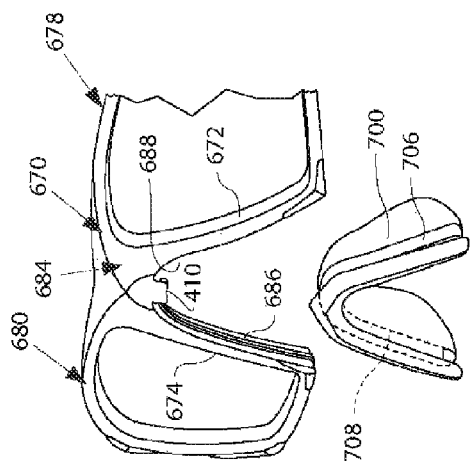
FIG. 30 is a perspective view of a nosepiece for use with the auxiliary frame of FIG. 29.

FIG. 30 illustrates a modified nosepiece 810 for fitment to the auxiliary frame 770 and installation onto a protective shield such as shown in FIG. 25. The nosepiece 410 includes openings 812, 814 for receiving the protrusions 772, 774, and a top slot 816 for receiving the tab 410 and tang 416.

FIG. 32 illustrates an auxiliary frame 900 that is substantially identical to the frame 370 shown in FIGS. 19 and 20 except that the bridge area 904 has a somewhat different shape.

FIGS. 33 and 34 illustrate an alternate adapter 920 that is similar to the adapter 360 except that the guides 432, 434 are not used and sides 924, 926 of the adapter 920 are substantially linear. The auxiliary frame 900 is mounted and secured to the adapter 920 using the tab 410 combined with a close fitting or frictional arrangement between the sides 930, 932 of the auxiliary frame 900 (FIG. 32) and the sides 924, 926 of the adapter. The adapter is mounted to the goggles in the same manner as is the adapter 360.

It can be recognized that for any of the eyewear embodiments described in this specification, the outer protective shield or goggle can be worn without the auxiliary lens or lenses, for example, if prescription eyewear is not needed. In the embodiment illustrated in FIG. 10, for example, if no auxiliary lens is desired, the adapter 360 need not be installed.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A protective eyewear, comprising:
a protective eyewear frame comprising a frame opening for holding a protective lens, a front face region, a top wall region adjacent said front face region, sidewall regions, and bottom wall regions, said top wall region having substantially vertically directed ventilation openings, said sidewall regions comprising substantially horizontally directed ventilation openings, said front face region including at least one substantially horizontally directed front ventilation opening that direct outside air through the front face region to an top area open to outside air and located above the substantially vertically directed ventilation openings of the top wall region;
strap anchor portions adjacent said sidewall regions that provide attachments for mounting the protective frame to a user's head, wherein said strap anchor portions include angled louvers for directing air inwardly toward said horizontally directed ventilation openings of said sidewall regions; and
a protective lens mounted to said frame opening.

2. The protective eyewear according to claim 1, comprising an auxiliary frame holding at least one auxiliary lens, said auxiliary frame mounted beneath said top wall region of said protective frame, said auxiliary frame having a downwardly extended tab and said protective frame having a slot arranged to receive said tab to removably attach said auxiliary frame to said protective frame.

3. The protective eyewear according to claim 2 wherein said downwardly extended tab includes a horizontally extended tang for locking said tab into said slot.

4. The protective eyewear according to claim 1 wherein said protective frame includes grip warts for gripping and manipulating the protective eyewear.

5. The protective eyewear according to claim 4 wherein said bottom wall regions of said protective frame comprise a soft material and said grip warts are formed to extended outwardly from said bottom wall regions, and said strap anchor portions comprise separate parts that are of a relatively harder material, said strap anchor portions include openings for receiving said grip warts and said grip warts have a height sufficient to extended outwardly of said strap anchor portions.

6. A protective eyewear, comprising:
a protective eyewear frame comprising a frame opening for holding a protective lens, a front face region, a top wall region adjacent said front face region, sidewall regions, and bottom wall regions, said protective frame includes grip warts being in the form of raised bumps projecting down from flat surface of the bottom wall regions for assisting the gripping and manipulation of the protective eyewear; and
a protective lens mounted to said frame opening.

7. The protective eyewear according to claim 6, wherein said front face region includes strap anchor portions that provide attachments for mounting the protective frame to a user's head, wherein said strap anchor portions include louvers for directing air inwardly toward horizontally directed ventilation openings of said sidewall regions.

8. The protective eyewear according to claim 6, wherein said grip warts extend vertically downward from a bottom of said frame.

9. A protective eyewear, comprising:
a protective eyewear frame comprising a frame opening for holding a protective lens;
a pair of strap anchor portions that provide attachments for mounting the protective frame to a user's head, said strap anchor portions being of a harder material than said frame, said strap anchor portions fixedly secured to said frame by tabs and holes applied between said strap anchor portions and said frame; and
a protective lens mounted to said frame opening.

10. The protective eyewear according to claim 9, wherein said engagement between said tabs and holes is at least partially secured by the subsequent installation of said protective lens to said frame opening.

11. The protective eyewear according to claim 9, wherein said strap anchor portions include at least one louver for directing air inwardly toward horizontally directed ventilation openings through said frame.

12. The protective eyewear according to claim 9, wherein the lens imparts rigidity to the frame and secures the engagement between the tabs and holes.

13. The protective eyewear according to claim 9 wherein said strap anchor portions include at least one louver for directing air inwardly.

* * * * *